United States Patent [19]

Upsher

[11] 4,406,280
[45] Sep. 27, 1983

[54] LARYNGOSCOPE INCLUDING A DISPOSABLE BLADE AND ITS METHOD OF USE

[76] Inventor: Michael S. Upsher, 2957 Adeline Dr., Burlingame, Calif. 94010

[21] Appl. No.: 311,990

[22] Filed: Oct. 16, 1981

[51] Int. Cl.³ .............................................. A61B 1/06
[52] U.S. Cl. .............................................. 128/11
[58] Field of Search ...................... 128/6–11, 128/13, 16, 18, 22, 23, 787, 788, 303.13, 303.14, 303.17, 303.18; 339/80, 95 R

[56] References Cited

U.S. PATENT DOCUMENTS

| | | | |
|---|---|---|---|
| 2,289,226 | 7/1942 | Foregger | 128/11 |
| 3,281,637 | 10/1966 | Hultquist | 128/9 |
| 3,426,749 | 2/1969 | Jephcott | 128/11 |
| 3,739,769 | 6/1973 | Kaye | 128/6 |
| 3,949,740 | 4/1976 | Twentier | 128/9 |
| 4,273,112 | 6/1981 | Heine et al. | 128/11 |

FOREIGN PATENT DOCUMENTS 2147054 4/1973 Fed. Rep. of Germany ........ 128/11
2361855 3/1978 France .................................. 128/11

Primary Examiner—Kyle L. Howell
Assistant Examiner—Max F. Hindenburg
Attorney, Agent, or Firm—Flehr, Hohbach, Test, Albritton & Herbert

[57] ABSTRACT

A laryngoscope is disclosed herein and includes a handle and a separate disposable blade which is designed to incorporate a number of specific features. One of these features resides in the way in which the blade is disengagably connected to its associated handle for the first time so as to damage a component of the blade sufficient to discourage its use a second time, but without preventing it from being used in the proper way the first time. In accordance with another feature, the blade includes an integrally formed main body which defines an open ended passageway for containing a light guide. This passageway is configured to define the arc of a circle so that the blade body including this passageway can be manufactured by means of an uncomplicated molding process.

37 Claims, 16 Drawing Figures

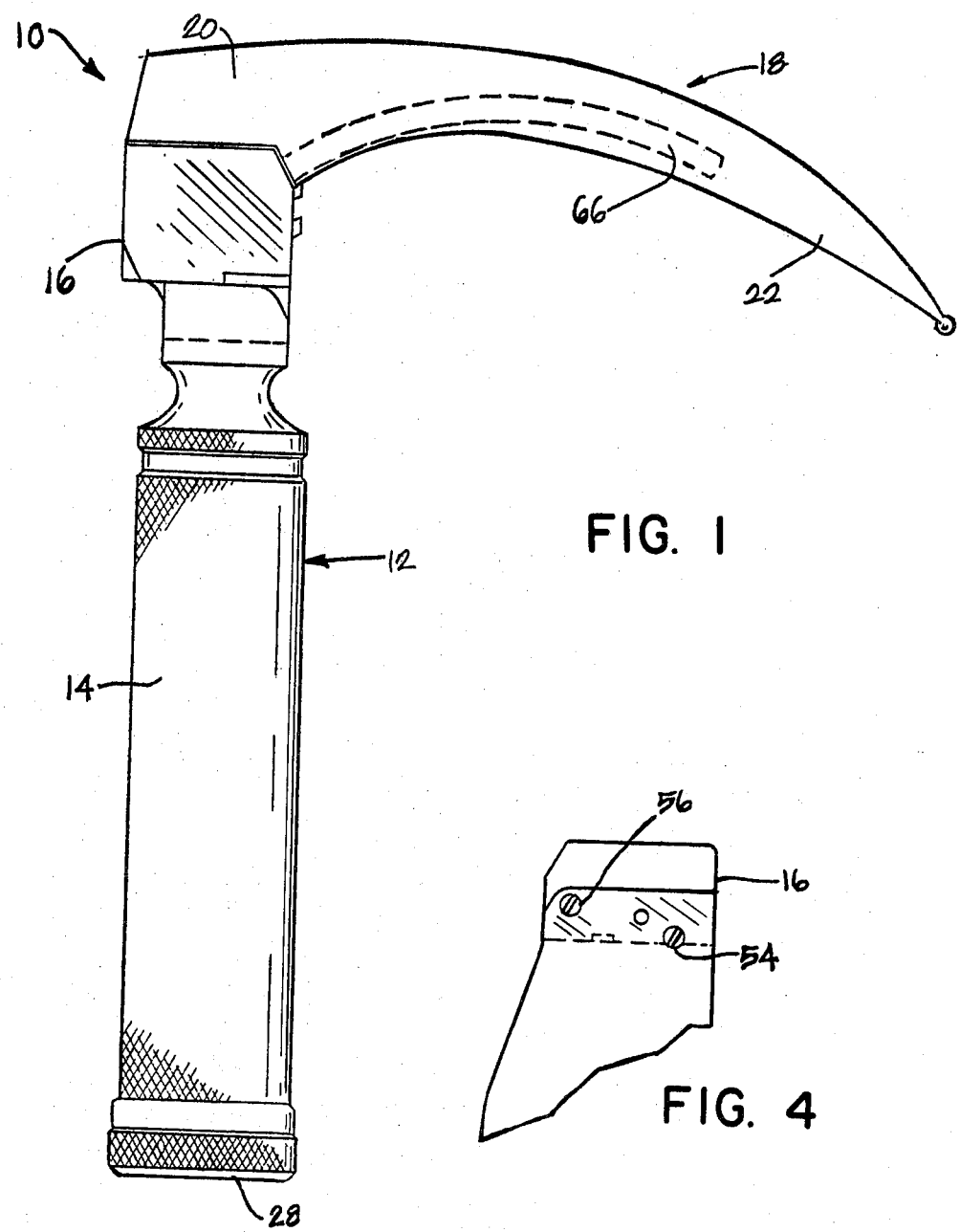

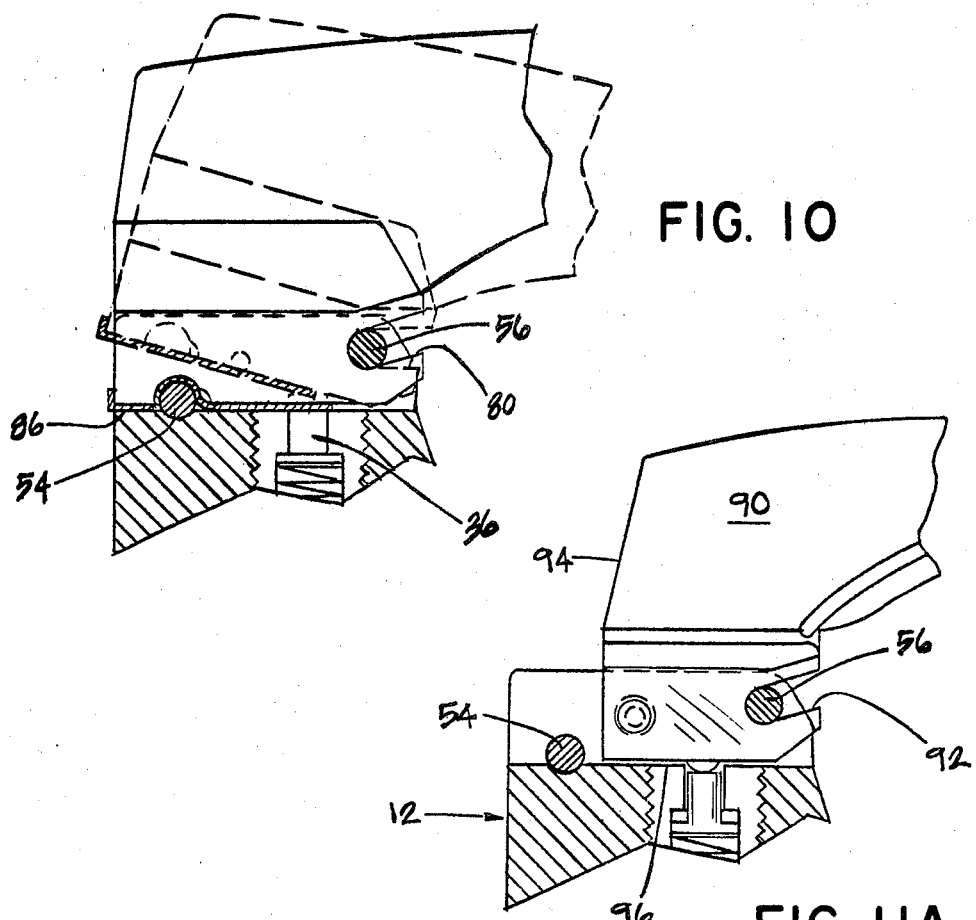
FIG. 10
FIG. 11A
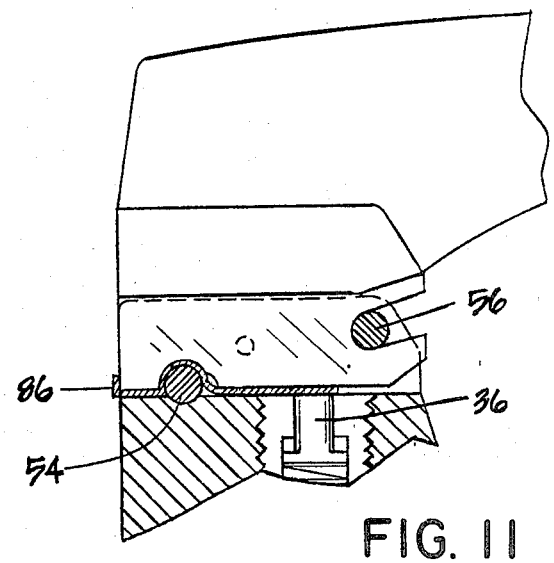
FIG. 11

LARYNGOSCOPE INCLUDING A DISPOSABLE BLADE AND ITS METHOD OF USE

The present invention relates generally to laryngoscopes and more particularly to a laryngoscope which utilizes a specifically designed disposable blade.

There are presently a number of generally similar types of laryngoscopes available in the prior art. The typical laryngoscope available includes an elongated handle, a separate blade for use on the handle, and an arrangement carried partially by the handle and partially by the blade for producing a beam of light in a predetermined direction relative to the blade. This latter arrangement utilizes a power supply contained within the handle for energizing a light source which produces the beam just recited. In most laryngoscopes, the light source is supported by and forms part of the blade, although in one type of laryngoscope presently being used the light source is carried by and forms part of the handle and cooperates with a light pipe on the blade. In either case, the handle and blade include cooperating means for disengagably connecting the two together so as to cause the power supply to energize the light source and cause the resultant beam to be pointed in the desired direction relative to the blade.

While laryngoscopes of the type described are generally satisfactory for their intended use, applicant has found that continued use of the same laryngoscope blade (1) requires sterilization which can be a costly procedure and (2) can result in cross-infection between patients. Accordingly, a primary object of the present invention is to provide a laryngoscope including a blade which is specifically designed to be disposable.

Another object of the present invention is to provide a disposable laryngoscope blade which is economical to manufacture and reliable to use.

Still another object of the present invention is to provide a disposable laryngoscope blade and associated handle which are designed to cooperate with one another so as to specifically discourage use of the blade more than once, but without interfering with its proper use the first time.

Yet another object of the present invention is to provide a laryngoscope including a handle and a disposable blade of the above-mentioned type as well as a compatibly but economically provided arrangement for producing an associated beam of light for purposes of observation.

As will be described in more detail hereinafter, the laryngoscope disclosed herein includes a handle and a disposable blade. The handle has an elongated hand gripping portion and a blade connecting head portion and the blade includes a handle connecting segment and an elongated tongue holding segment connected with and extending out from the handle connecting segment. A first arrangement carried partially by the handle and partially by the blade are provided in order to produce a beam of light in a predetermined direction relative to the tongue holding segment of the blade for purposes of observation when the blade is connected with the handle in a specific way. A second arrangement forming parts of the handle and the blade cooperate to disengagably connect the two together so as to cause the observation beam to be produced.

In accordance with one feature of the present invention, the cooperating arrangement just recited not only causes the observation beam to be produced, but when the blade is connected to the handle for the first time this arrangement causes a component of the blade to be damaged sufficient to discourage use of the blade a second time without preventing it from being used in the proper way the first time.

In accordance with another feature of the present invention, the handle connecting and tongue holding segments of the blade are integrally molded as a single member which provides an elongated, open ended passageway configured to define an arc of a circle within a single plane. In this way, the passageway can be economically and reliably molded into the integral member using a core puller. A light guide is contained within the passageway and forms part of the arrangement for producing the previously recited beam of light.

These and other features of the laryngoscope disclosed herein will be discussed in detail hereinafter in conjunction with the drawings, wherein:

FIG. 1 is a side elevational view of a laryngoscope including a handle and disposable blade as well as other associated components designed in accordance with the present invention;

FIG. 4 is an opposite side elevational view of a top portion of the handle illustrated in FIGS. 2 and 3;

FIG. 10 is a partially broken away, side elevational view illustrating a top portion of the laryngoscope handle of FIG. 1 and a back end segment of the blade showing how the latter is disengagably connected to the handle in accordance with the present invention;

FIG. 11 is a view similar to FIG. 10 but shows the laryngoscope blade in its disengagably connected position with respect to the handle;

FIG. 11A is a view similar to FIG. 11 but shows a prior art blade disengagably connected to the handle illustrated in FIGS. 2-4;

Figure 3:
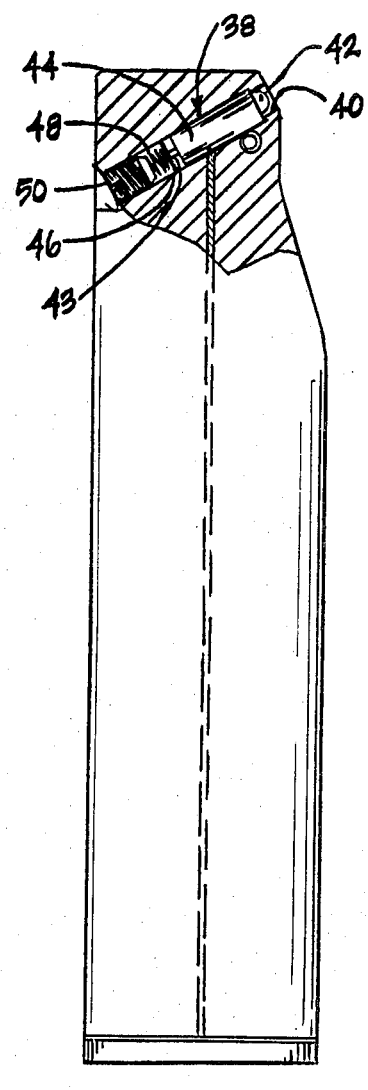
FIG. 3 is a partially broken away side elevational view of the handle and its associated components shown in FIG. 2.

Turning now to the drawings, wherein like components are designated by like reference numerals throughout the various figures, attention is first directed to FIG. 1 which illustrates a laryngoscope 10 designed in accordance with the present invention. This laryngoscope includes a handle 12 which may be divided into two functional portions, an elongated hand gripping portion 14 and a blade connecting head portion 16. The laryngoscope also includes a disposable blade 18 which is separate from the handle and which may be functionally divided into two segments, a handle connecting back end segment 20 and an elongated tongue holding segment 22 connected with and extending out from segment 20. In addition to handle 12 and disposable blade 18, laryngoscope 10 includes a number of associated components which together form a first arrangement for producing a beam of light in a predetermined direction relative to the blade when the latter is connected to the handle in a specific way and a second arrangement forming part of the blade and part of the handle for disengagably connecting the two together in a way which (1) produces the beam and (2) discourages use of the disposable blade more than once.

Figure 2:
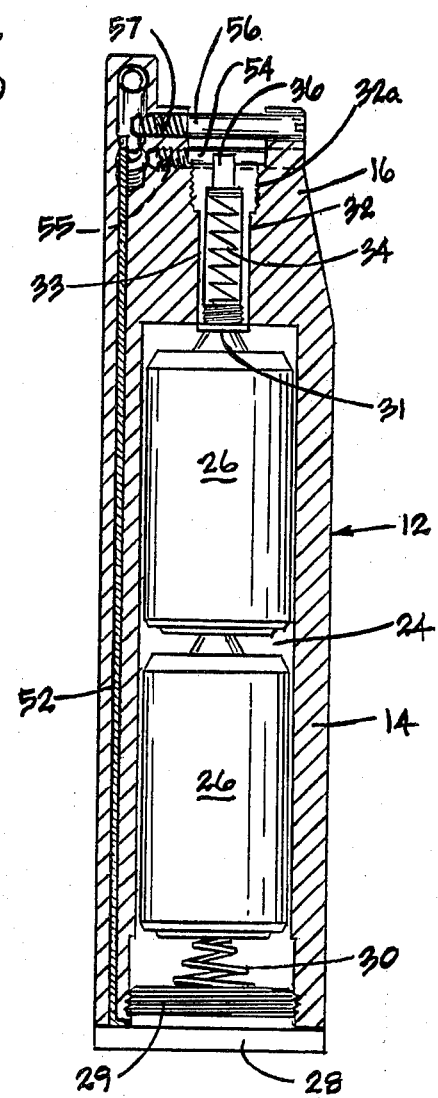
FIG. 2 is a front longitudinal sectional view of the handle and certain associated components forming part of the laryngoscope of FIG. 1.

Referring to FIGS. 2-4, 10 and 11 in conjunction with FIG. 1, attention is directed to handle 12 and a number of components forming part of the beam producing arrangement just recited. As illustrated specifically in FIGS. 2 and 3, the hand gripping portion 14 includes an interior chamber 24 which is opened at the bottom end of the handle for receiving and containing two series connected batteries 26. The bottom end of the container is sealed by means of an end cap 28 having an inner electrically conductive section 29 which is electrically connected to an adjacent battery 26 by means of an electrically conductive spring member 30. The spring member also serves to urge the two batteries in a vertically upward direction (as viewed in FIG. 2) against an electrically conductive contact 31 at the bottom opened end a stem or sleeve member 32. This latter member is contained within a cooperating internal opening 33 in end portion 16 of handle 12 and extends patially into chamber 24 as seen in FIG. 2. A top end section 32a of sleeve 32 and a corresponding top end section of opening 33 are threaded in order to maintain the sleeve in place. In this regard, the top of the sleeve is slotted (not shown) to facilitate a screwdriver. The top end of contact 31 engages a second electrically conductive spring 34 which is also disposed within sleeve 32 and which extends up through and along the entire length of the sleeve. The top end of spring 34 engages and supports an electrically conductive actuating pin 36 for movement between a biased extended position illustrated in FIG. 2 (and by dotted lines in FIGS. 10 and 11) and a retracted position illustrated by solid lines in FIGS. 10 and 11. When the pin 36 is in its extended position, it extends through a cooperating opening in the top end of sleeve 33. The batteries 26, section 29 of end cap 28 and its associated spring 30, the spring 34 and its associated actuator pin 36 together form part of the beam producing arrangement referred to above.

The beam producing arrangement also includes a suitable source of light, specifically the assembly generally indicated at 38 contained within a cooperating opening 40 in handle portion 16. Assembly 38 is composed of a conventional bulb 42 having a hot side contact 43 and a ground side contact (its body) contained within an electrically conductive grounding sleeve 44. The bulb body is maintained in electrical contact with the sleeve by means (not shown) within the sleeve. At the same time, contact 43 is engaged by a contact element 46 which is spring-loaded using the spring 48 and set screw 50, the latter also serving to close the back end of opening 40. The front end of opening 40 is left unobstructed so as to provide ready access to bulb 42. As illustrated in FIGS. 2 and 3, sleeve 44 is electrically connected to end cap section 29 by means of a ground wire 52 contained within and extending the length of handle 12 between the sleeve and end cap.

Referring specifically to FIGS. 10 and 11 in conjunction with FIG. 2, the beam producing arrangement including the various components thus far described also includes a horizontally extending, fixed pin 54 which is disposed within a cooperating groove in the top of handle portion 16 and partially exposed at the top end of the handle. As best seen in FIG. 2, the inwardmost end of pin 54 physically engages set screw 50 which means that pin 54 is in electrical contact with contact 46 which is in electrical contact with hot side contact 43 of bulb 42 and hence in electrical circuit with batteries 26 through the bulb filament and jacket and ground wire 52. Pin 54 is preferably threaded along its inward end section 58 adjacent set screw 50 and the opening in handle portion 16 containing this threaded end section is also threaded in a cooperating fashion. The opposite end of pin 54 is preferably slotted as seen in FIG. 4 so that a standard screwdriver can be used to place the pin in its proper position.

Pin 54 not only forms part of the beam producing arrangement but also serves as part of the previously recited arrangement for disengagably connecting blade 18 to handle 12. To this end, and for the reasons to be discussed, pin 54 is circular in cross section and is disposed a predetermined distance behind pin 36, as best seen in FIGS. 10 and 11. As also seen in these latter figures, a second horizontally extending cylindrical pin 56 is supported on and forms part of handle 16 immediately in front of and slightly above vertical pin 36. Pin 56 also forms part of the blade connecting arrangement just mentioned. At the same time, it serves as part of an alternate electrical circuit including batteries 26, pin 36 and bulb 42 but not including pin 54, as will be discussed hereinafter. For this reason, one end of pin 56, specifically its threaded end 57 which is contained within a cooperating threaded opening in the handle portion 16 is retained in physical engagement with bulb sleeve 44. The other end of pin 56 is slotted in order to place it in its operating position.

Figure 6:
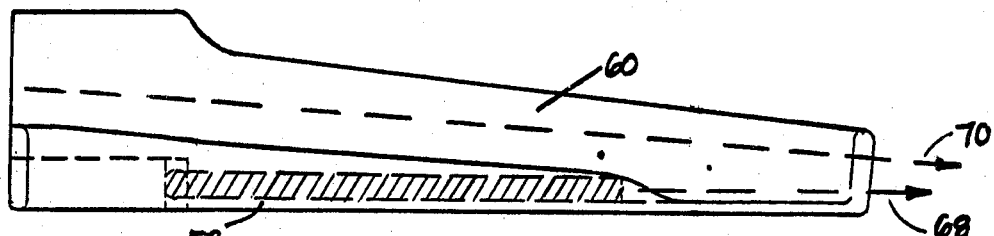
FIG. 6 is a top plan view of the blade and associated components illustrated in FIG. 5.
Figure 5:
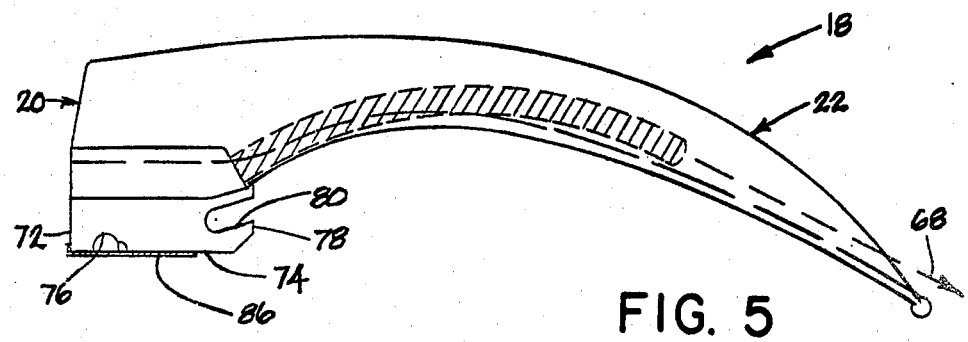
FIG. 5 is a side elevational view of the laryngoscope blade and certain associated components forming part of the laryngoscope of FIG. 1.
Figure 7:
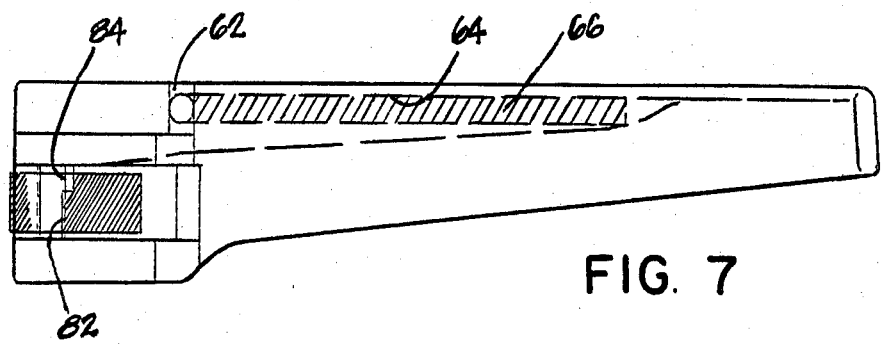
FIG. 7 is a bottom plan view of the blade and associated components shown in FIG. 5.
Figure 8:
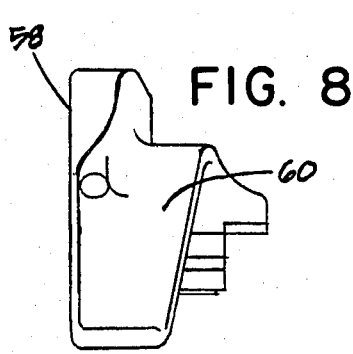
FIG. 8 is a front elevational view of the blade and associated components in FIG. 5.
Figure 9:
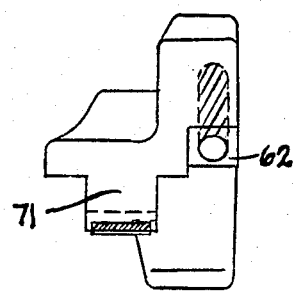
FIG. 9 is a back elevational view of the blade and associated components shown in FIG. 5.

Referring now to FIGS. 5-9, attention is directed to disposable blade 18. As stated previously, this blade includes a handle connecting segment 20 and an elongated tongue holding segment 22 connected with and extending out from the handle connecting segment. In a preferred embodiment, these two segments are integrally formed as a single member by means of injection molding or the like and may be constructed of any material compatible with its method of manufacture, preferably hard plastic, for example, polycarbonate. As best illustrated in FIGS. 6 and 8, tongue holding segment 22 may be divided into two lengthwise sections, a tongue blocking and light guide holding section 58 forming a lengthwise side of segment 22 and a viewing and anesthesia tube guiding section 60 forming the other lengthwise side of the segment. Section 58 terminates rearwardly at a planar shoulder 62 (see FIGS. 7 and 9) which forms part of handle connecting segment 20. For reasons to become apparent hereinafter, shoulder 62 is disposed at an angle of about 30° with the vertical, that is, perpendicular to the axis of passageway 40 in blade connecting head portion 16 of handle 12 which means that shoulder 62 is perpendicular to the beam axis of light source assembly 38.

Section 58 of blade segment 22 includes an open ended, internal passageway 64 extending from the rearward end of the section at shoulder 62 to its front end which is best illustrated in FIG. 8. This passageway is configured to define an arc of a circle (see FIG. 5) which lies within a single plane (see FIGS. 6 and 7). This passageway serves to contain a light guide 66, for example, an optical fiber, a bundle of optical fibers, or the like, extending the entire length of the passageway. In an actual embodiment, a single rod of acrylic was used successfully. As will be seen hereinafter, light guide 66 cooperates with the light source 42 when blade 18 is connected with handle 12 for directing the beam produced by the light source in a predetermined direction relative to the blade, specifically, in the direction of arrow 68 illustrated in FIGS. 5 and 6. This light is used to illuminate a patient's throat during the initial anesthesiology workup while section 58 of the blade holds the tongue to one side. As a result, the anesthesiologist is provided with a clear view into the laryngeal area of the patient along section 60 and he may use this latter section as a guide to insert the anesthetic tube or tubes (not shown) into position.

The passageway 64 was described above as defining an arc of a circle. While blade 18 is not limited to this particular configuration, it is preferred for ease of manufacture when the blade is of the Macintosh type, e.g., curved. More specifically, by making the passageway truly arcuate and particularly less than that of a half circle, passageway 64 can be molded into the blade segments 20 and 22 as these segments are molded into a single member using a suitable shaped core puller. This cannot be done if the passageway is not either straight or truly arcuate since the core puller could not be removed once a curved but not arcuate passageway is formed. Because of the desired arcuate configuration of passageway 64 and therefore light guide 66, the latter cannot be bent out of its arcuate configuration to better coincide with section 60 during observation of the patient's larynx. Therefore, as best illustrated in FIG. 6, section 60 is designed to extend at an acute angle with section 58 so that the observation angle along section 60, as indicated by arrow 70, is at an acute angle with light beam 68. In this way, the light beam more efficiently illuminates the area being observed.

Having described segment 22 of blade 18 and its associated light guide 66, attention is now directed to segment 20. As illustrated in FIGS. 5 through 9, this segment includes a rearward projection 71 having a vertically extending, flat back end 72 which is positioned directly behind section 60 of blade segment 22. Directly below section 60 and joining back end 72 is a horizontally extending, flat bottom 74 which contains a downwardly opening slot 76 to be discussed below. Opposite back end 72 and extending up from bottom 74 is a front end 78 of blade segment 20. Front end 78 includes an inwardly extending and slightly downwardly angled slot 80 (see FIG. 5) extending across its entire width (see FIG. 7). The slot 76 also extends the entire width of projection 71 (again, see FIG. 7) and for reasons to be discussed hereinafter, the cross sectional configuration of this latter slot defines an arc of a circle which is slightly greater than a half circle. The forward edge of this slot is designed to provide a relative sharp, knife edge 82 along a portion of its length from one end thereof. The rest of the same edge is recessed as indicated at 84 therefore eliminating a cutting edge at that point. The entire slot 76 and a portion of bottom 74 are covered by an electrically conductive foil 86 bonded to bottom 78 or other electrically conductive means. For reasons to be discussed, the foil or other such means is readily severable in the way to be described.

Having now described laryngoscope blade 18 in its entirety from a structural standpoint, attention is directed to the way in which this blade is connected and interacts with handle 12, as best illustrated in FIGS. 10 and 11. As seen there, blade segment 20 is initially disposed over the top end of handle 12 at an angle with the latter. Pin 56 forming part of the blade connecting head portion 16 is located in slot 80 and is used as a means for pivoting the blade between the angled position illustrated in FIG. 10 and the flat operating position illustrated in FIG. 11. As blade segment 20 moves from its FIG. 10 position to its FIG. 11 position, a front end of foil 86 engages against and remains in contact with pin 36 as the latter is pushed down into its retracted position. At the same time, slot 76 is forced into snap fitting engagement around pin 54. In this latter regard, as stated previously, the diameter of slot 76 is approximately equal to the diameter of pin 54 but the cross section of the slot is greater than a half circle. Moreover, projection 71 which is preferably plastic is sufficiently resilient to provide a limited degree of give to slot 76 so that the latter can snap around and interlock with pin 54 upon application of sufficient force. At the same time, cutting edge 82 severs a corresponding length of the foil (or other such means) across the width of the latter. However, because of recess 84, foil 86 is not entirely severed. Thus, with blade 18 mounted on handle 12 in the manner illustrated in FIG. 11, foil 86 serves as an electrical connection between pins 36 and 54. This, in turn, closes the electrical circuit between batteries 26 and light bulb 42 causing the latter to be energized for producing a beam of light. At the same time, the foil is sufficiently damaged as a result of being partially severed so as to discourage anyone from using the disposable blade a second time. While foil is preferred to accomplish this, it is to be understood that other means serving the same function could be used.

From the foregoing, it should be apparent that the pins 36, 54 and 56 form a part of handle portion 16 and the slots 76 and 80 and foil 86 forming part of blade segment 20 cooperate with one another for disengagably connecting the disposable blade to the handle in a specific way so as to energize light bulb 42. At the same time, when the blade is used for the first time, a component thereof is damaged, specifically foil 86, sufficient to discourage anyone from using the blade a second time, but without preventing it from being used in the proper way the first time. In addition, placement of the laryngoscope blade on its handle in the appropriate way automatically places planar shoulder 62 and the back end of light guide 66 in confronting relationship with and across the front or opening 40 and light bulb 42. In this way, light guide 66 is able to capture and collect substantially all of the light beam passing out of the opening 40 from the light bulb for directing this beam in the direction of arrow 68. This is accomplished without having to provide a 90° bend in the light guide and yet the light is ultimately directed in the most beneficial direction relative to the blade segment 22. Moreover, this has been found most easily accomplished by orienting opening 40 and therefore the axis of the light beam leaving this opening at an angle of 30° with a plane normal to the axis of handle portion 14, that is, with the horizontal when the handle portion is held in a vertical direction.

Having described laryngoscope 10, it should be apparent that the blade 18 can be made relatively economically by molding the segments 20 and 22 as a single integral member with the passageway 64 being formed of the same time. In this way, in order to complete the blade, all that is necessary is that the light guide be inserted into the passageway and that the foil 86 be adhered to bottom 74 of projection 71. Moreover, all of these components are relatively inexpensive and therefore the overall blade is disposable after a single use. To this end, by partially severing the foil when the blade is first used, its user is encouraged to dispose of it thereafter.

Because of the way in which blade 18 is designed, handle 14 is different than the typical prior art handle, at least to the extent that handle 14 includes pin 54 in circuit with batteries 26 and bulb 42. In the typical prior art handle, no such pin exists. Rather, the prior art handle utilizes a pin corresponding to pin 56 (and the rest of the blade body) in conjunction with a pin corresponding with pin 36 to close the electrical circuit between its batteries and associated light source and the latter is typically carried by the blade rather than the handle. In this latter case, the light source is connected in circuit with an insulated button on the blade which makes contact with pin 36. At the same time, the rest of the blade including pin 56 makes contact with the handle body and serves as a ground. FIG. 11A illustrates the back end of a conventional metal laryngoscope blade generally indicated at 90. The handle connecting back end segment of this blade includes a front slot 92 corresponding to previously described slot 80, a back end 94 and a bottom 96. This handle connecting segment can be mounted to the top end of handle 12 by placing pin 56 in slot 92 and pivoting the blade about the axis of this latter pin until the bottom 96 rests against pin 36 and causes this pin to move to its retracted position. This, in turn, incorporates the batteries 26 into and closes an electrical circuit including a light source associated with and carried by the blade 90 for energizing the light source. However, it should be noted that the pin 54 is positioned relative to pin 36 such that the back end 94 of blade 90 does not engage this rearward pin. Therefore, when prior art blade 90 is disengagably connected to handle 12, bulb 42 carried by the handle is not energized and therefore does not unnecessarily drain the batteries or needlessly withdraw power from the other, intended light source.

Figure 12:
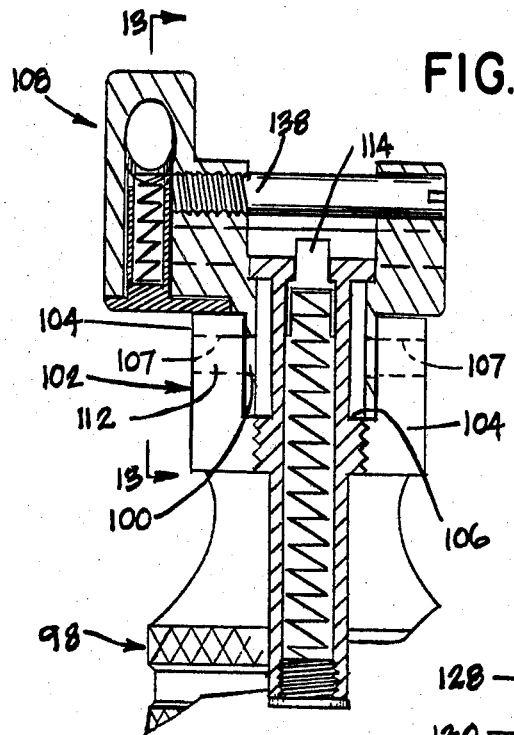
FIG. 12 is a front elevational view of a top portion of a laryngoscope including a prior art handle and an arrangement for adapting the handle for use with the laryngoscope blade illustrated in FIGS. 5-9.

Having described the way in which handle 12 forming part of a laryngoscope 10 cooperates with a prior art blade, attention is now directed to the way in which the prior art handle can be readily converted to one which will operate with blade 18 in the same manner as handle 12. The top end of this prior art handle is generally illustrated in FIG. 12 at 98. While not shown, the bottom end of the handle may be identical to handle portion 14 and includes similar batteries 26. The top end of the handle includes a pin 100 which corresponds to pin 56 of handle 12 that is, it is the pin which is disposed within the slot corresponding to slot 92 of prior art blade 94. While not shown, this conventional handle also includes a vertically extending pin and associated component corresponding to pin 36 and components 32 and 34 (see FIG. 2). However, in order to adapt handle 98 to include blade 18, this latter pin and its associated components are removed and entirely eliminated and the pin 100 is temporarily disassembled from the blade connecting head portion 102 forming the top end of the handle. This leaves a pair of spaced apart flanges 104 having aligned through holes 107 extending vertically upward at the top end of the handle across which pin 100 is supported. With the pin disassembled therefrom, a threaded opening 106A into the base 106 of portion 102 is made accessible. This opening extends all the way down to the chamber in the handle containing the batteries corresponding to batteries 26.

With portion 102 of handle 98 in the condition just recited, an adapter generally indicated at 108 is mounted on and connected with the handle portion. This adapter may be separated into two components, a main body 108A shown alone in FIG. 15A and a shaft arrangement 108B shown alone in FIG. 15B. Main body 108A includes a lowermost base section 110 (see FIGS. 13 and 15A) which includes a vertically extending unthreaded through hole 111, which fits snugly between flanges 104 (see FIG. 12) and which includes a horizontal through hole 112 in alignment with the through hole 107 of flanges 104. In this way, the pin 100 can be reassembled into its corresponding openings 107 and, at the same time, through opening 112 for holding the adapter in place. Also, the hole 111 is automatically placed in vertical alignment with and above threaded hole 106A in the handle.

Figure 14:
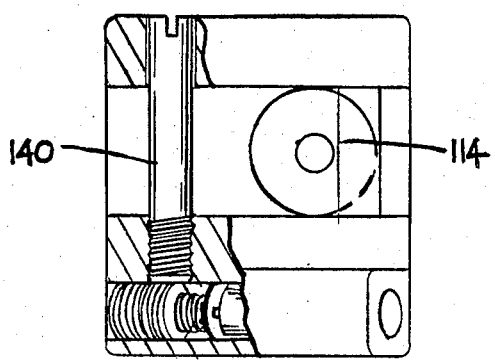
Figure 15:
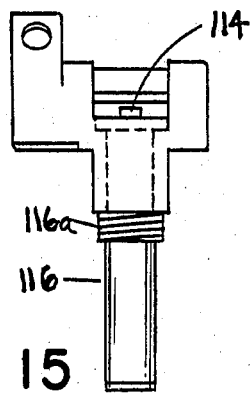
Figure 15A:
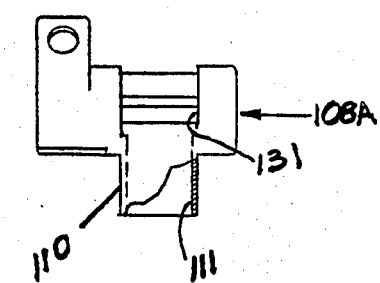
Figure 15B:
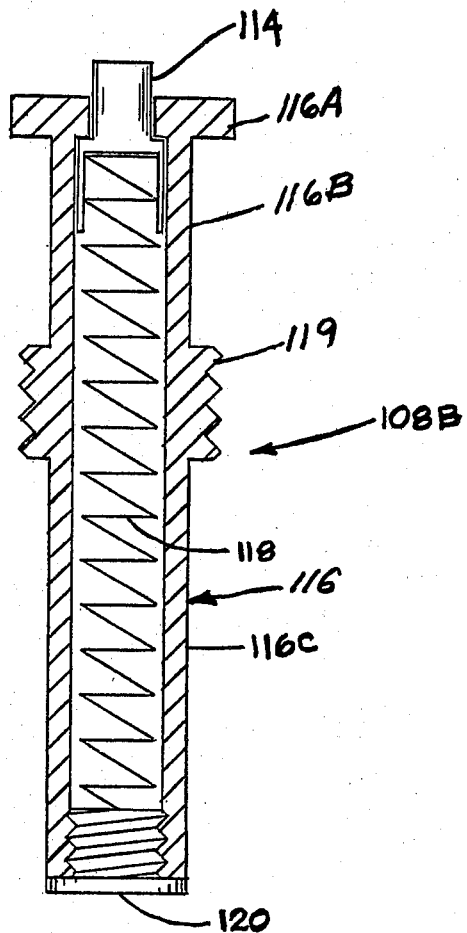
Figure 16:
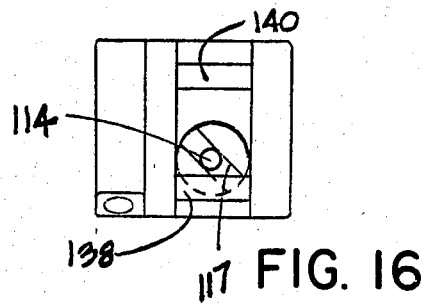

As best illustrated in FIGS. 14, 15B and 16, shaft arrangement 108B includes its own vertically extending pin 114 corresponding in function to pin 36 disposed within a sleeve 116 corresponding to sleeve 32. As seen in FIG. 15B, the sleeve 116 includes an enlarged head 116A which is slotted at 117 (see FIG. 16), an intermediate section 116B which is threaded at 119 and a norrower bottom portion 116C. A spring 118 is also located within sleeve 16 between pin 114 and a lowermost contact 120 which is thread connected into and through a cooperating threaded opening 122 in the bottom of sleeve 116. The lowermost unthreaded end of sleeve 116 is provided for maintaining pin 114 in electrical contact with the batteries in handle 98 when the adapter is in place on top of the handle. In this regard, the bottom portion 116C and the threaded section 119 of portion 116B of the shaft 116 are placed through hole 111 in main body 108A. The threaded section 119 cooperates with threaded hole 106A in base 106 of handle 98 so that contact 120 engages the batteries in the handle. In this latter regard, the slot 117 in enlarged head 116A is used to thread connect section 119 with threaded opening 106A until the head moves into a cooperating recess 131 in main body 108A (see FIG. 15A). Thus, the bottom threaded section 119 of sleeve 116 in FIG. 15 is thread connected into the opening in base 106 for connecting the adapter to the handle. Pin 114, the spring 118 and contact 120 together function in the same manner as the pin 36 and its associated components 31, 32 and 34.

Figure 13:
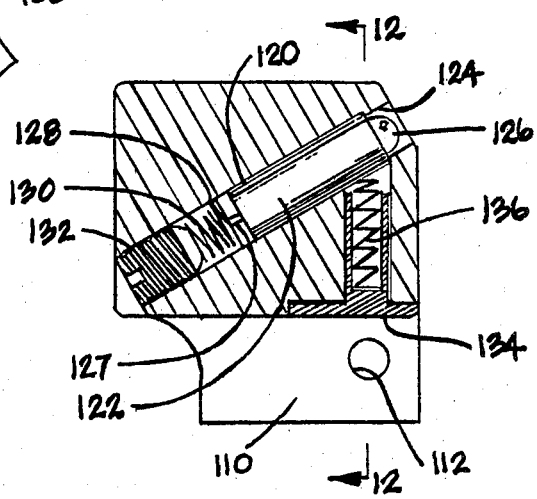
FIGS. 13-16 are various views of the adapter arrangement illustrated in FIG. 12.

Referring specifically to FIGS. 12-14, the adapter's main body 108A is shown including a light source assembly 120 which may be identical to the previously described assembly 44. Thus, assembly 120 includes a metal grounding sleeve 122, contained within an open ended passageway 124 in the adapter and housing the light bulb 126 which remains in place by means of a shoulder at its forwardmost end. A hot side contact 129 on the bulb, a contact 128, an associated spring 130 and adjacent set screw 132 are provided and correspond to the components 43, 46, 48 and 50 in FIG. 3. In addition, the adapter includes a grounding rivet 134 which contains and is in electrical contact with a spring 136. The spring also engages against sleeve 122, thus placing the ground side of light bulb in electrical contact with the sleeve.

In addition to the various components thus far described, adapter 108 includes a front pin 138 disposed in front of and slightly above pin 114 (see FIG. 14) and a back pin 140 positioned directly behind pin 114. The pin 138 corresponds in function and structure to previously described pin 56 and the pin 140 corresponds in function and structure to pin 54. In other words, the three pins 114, 138 and 140 respectively serve the same purposes as the pins 36, 56 and 54 in supporting laryngoscope blade 18. In order to provide the appropriate electrical connections between these various components, the pin 138 is designed to engage the rivet 134 as illustrated in FIG. 12. This places pin 138 in electrical contact with sleeve 122 and therefore the ground side of bulb 126. The pin 140 physically engages the set screw 132 (see FIG. 14), thereby placing pin 140 in electrical contact with the hot side contact 127 of bulb 126. By providing the combination rivet 123 and spring 136, it is not necessary to directly engage against sleeve 122 with pin 138, thereby minimizing damage to the latter. This is also true for pin 40 which engages the set screw 132 rather than sleeve 122.

What is claimed is:

1. A laryngoscope comprising:
   (a) a handle including an elongated hand gripping portion and a blade connecting head portion;
   (b) a disposable blade separate from said handle and including a handle connecting segment and an elongated tongue holding segment connected with and extending out from said handle connecting segment;
   (c) means carried partially by said handle and partially by said blade for producing a beam of light in a predetermined direction relative to the tongue holding segment of said blade when said blade is connected with said handle in a specific way, said beam producing means including a light source and power supply; and
   (d) first and second cooperating means respectively forming parts of the head portion of said handle and the handle connecting segment of said blade for disengagably connecting said disposable blade to said handle in said specific way for the first time so as to cause said beam to be produced and so as to damage a component of said disposable blade sufficient to discourage its use a second time without preventing it from being used in the proper way the first time, said first and second cooperating means disengagably connecting said blade to said handle in said specific way for the first time so as to place said power supply in electrical circuit with said light source in order to produce said beam, said first and second cooperating means including a readily severable, electrically conductive member forming part of the electrical circuit between said power supply and said light source and means for severing a substantial part of said electrically conductive member as said blade is disengagably connected to said handle in said specific way for the first time.

2. A laryngoscope according to claim 1 wherein said lectrically conductive member is a relatively thin, longated strip of metal foil which extends between the ead portion of said handle and the handle connecting segment of said blade when the latter is connected to said handle in said specific way.

3. A laryngoscope according to claim 2 wherein said first cooperating means includes first and second electrically conductive circuit means forming electrically spaced-apart junctions in said electrical circuit and wherein said strip of foil forms part of said second cooperating means so as to electrically connect said junctions together when said handle in said specific way.

4. A laryngoscope according to claim 3 wherein said first circuit means includes a fixed pin serving as one of said junctions and wherein said second cooperating means includes a groove on the opposite side of said foil as said pin, said groove cooperating with said pin to carry out said severing of said foil while at the same time disengagably connecting said blade to said handle in said specific way.

5. A laryngoscope according to claim 4 wherein said pin has a circular cross section defined by a given radius and wherein the cross section of said groove is defined by an arc of a circle having approximately the same radius, said arc being sufficiently greater than a half-circle and the groove itself being slightly resilient whereby the groove can interlock around the pin, said groove also providing a cutting edge for severing said foil, said cutting edge being shorter than the width of said foil.

6. A laryngoscope according to claim 1 wherein said beam producing means includes a power supply and a light source carried by said handle and a light guide fixedly held by and extending between said head connecting and tongue holding segments of said blade so as to be placed in optical alignment with said light source for directing said beam in said predetermined direction when said blade is connected to said handle in a specific way.

7. A laryngoscope according to claim 6 wherein said blade segments are integrally formed as a single member having an elongated, open ended passageway configured in an arc of a circle disposed in a single plane, and wherein said light guide is formed from at least one elongated optical fiber and contained within said guideway.

8. A laryngoscope according to claim 7 wherein said integrally formed member is molded plastic.

9. A laryngoscope according to claim 7 wherein the tongue holding segment of said blade includes a section which extends at an acute angle with said light guide so as to cooperate with said light beam for exposing a patient's throat to view when the laryngoscope is in use and, at the same time, to illuminate the patient's throat with said beam.

10. A laryngoscope according to claim 7 wherein the end of said light guide adjacent the handle connecting segment of said blade is flat and extends normal to and coaxial with the axis of said light source when said blade is connected with said handle in said specific way.

11. A laryngoscope according to claim 7 wherein said handle is substantially straight and wherein said light source is positioned relative to said handle so that its axis is disposed at a 30° angle with plane normal to said handle.

12. A laryngoscope according to claim 6 including an additional blade having its own tongue holding segment carrying its own light source and a handle connecting segment including means for disengagably connecting said additional blade to said handle in a way which places said last mentioned light source in circuit with said power supply without placing said first mentioned light source in electrical circuit with said power supply.

13. A laryngoscope according to claim 1 wherein the blade connecting head portion of said handle is disengagably connected to the hand gripping portion of said handle, said head portion serving as an adapter for handles having original blade connecting head portions which are incompatible with said disposable blade.

14. A laryngoscope according to claim 13 wherein said hand gripping handle portion includes a threaded opening extending therein from its top end and wherein said head portion includes an elongate hollow at least partially threaded shaft extending into and in threaded engagement with said threaded opening in said handle gripping portion.

15. A laryngoscope according to claim 14 wherein said beam producing means includes a power supply contained within said hand gripping handle portion below its threaded opening and wherein said shaft contains longitudinally electrical contacts at opposite ends thereof and an electrically conductive spring therebetween, the lowermost one of said contacts being in contact with said power supply for placing the other contact in circuit therewith.

16. A laryngoscope according to claim 15 wherein said head portion includes a main body having a threaded opening therethrough for containing said shaft in thread connection therewith.

17. A disposable blade for use as part of a laryngoscope which also includes a handle having an elongated hand gripping portion and a blade connecting head portion, said disposable blade comprising:
(a) a handle connecting segment including means designed to cooperate with the blade connecting head portion of said handle for disengagably connecting the blade to the handle in a specific way so that when said blade is connected to said handle in said specific way for the first time a component of said blade is damaged sufficient to discourage use of the latter a second time, but without preventing it from being used in the proper way the first time, said blade component including a strip of electrically conductive metal foil connected with said handle connecting segment so as to be engagable against the blade connecting head portion of said handle when said blade is connected to said handle and said connecting means forming part of said handle connecting segment including means for severing a portion of said foil;
(b) an elongated tongue holding segment connected with and extending out from said handle connecting segment; and
(c) means carried by said blade and designed to cooperate with said handle for directing the beam of light in a predetermined direction relative to said tongue holding segment.

18. A disposable blade according to claim 17 wherein said connecting means forming part of the handle connecting segment of said blade includes a groove across which said foil extends, said groove including one edge serving as said severing means.

19. In a laryngoscope including a handle having a light source and a power supply and a disposable blade disengagably connectable to said handle, a method of using said blade for the first time, said method comprising the steps of:
(a) providing said blade with a segment designed to be disengagably connected with said handle and an electrically conductive component intended to be damaged, said component serving to electrically connect said power supply to said light source when said blade is mounted to said handle;
(b) disengagably connecting said blade to said handle for the first time so as to damage said component sufficient to discourage the use of said blade a second time, but without preventing it from electrically connecting said power supply to said light source the first time.

20. A laryngoscope, comprising:
(a) a handle having a hand gripping portion and a blade connecting head portion, said head portion including first and second electrically conductive contact members and dielectric means for electrically insulating said members from one another;
(b) a laryngoscope blade separate from said handle and having a handle connecting segment including means defining an electrically conductive path and an elongated tongue holding segment connected with and extending out from said handle connecting segment;
(c) first and second cooperating means respectively forming parts of the head portion of said handle and the handle connecting segment of said blade for disengagably connecting said blade to said handle in a specific way which automatically causes said electrically conductive path defining means to engage and electrically connect together said first and second members;
(d) an electrical light source carried by said handle;
(e) a power supply carried by said handle for energizing said light source when placed in electrical connection with the latter; and
(f) circuit means including said first and second electrically conductive members fixedly electrically connected with said power source and light source, respectively, such that electrically connecting said first and second members together automatically electrically connects said power supply to said light source for energizing the latter, said circuit means also including said electrically conductive path defining means for automatically electrically connecting said first and second conductive members together for placing said power supply in electrical connection with said light source in order to energize the latter, whereby disengagably connecting said blade to said handle in said specific way automatically causes said light source to be energized without the need for electrical switches.

21. A laryngoscope according to claim 20 wherein the hand gripping portion of said handle defines an inner chamber containing said power supply, wherein said first electrically conductive member includes a pin and means extending into said chamber for electrically connecting said pin in said power supply, and wherein said second electrically conductive member includes a bar and means for electrically connecting the latter with said light source.

22. A laryngoscope according to claim 21 wherein said bar also serves as part of said first cooperating means for disengagably connecting said blade to said handle.

23. A laryngoscope according to claim 20 wherein said blade has a dielectric main body and an electrically conductive strip of material attached thereto serving as said electrically conductive path defining means.

24. A laryngoscope according to claim 20 wherein said blade connecting head portion of said handle is an arrangement separate from said hand gripping portion but disengagably connected therewith.

25. A laryngoscope according to claim 24 wherein the hand gripping portion of said handle includes a threaded opening and wherein said blade connecting portion includes a threaded stem thread connected into said opening for disengagably connecting said blade connecting head portion with said hand gripping portion.

26. A laryngoscope, comprising:
(a) a handle having a hand gripping portion including an inner chamber and a blade connecting head portion, said head portion including first and second electrically conductive members electrically insulated from one another;
(b) a laryngoscope blade separate from said handle and having a handle connecting segment including means defining an electrically conductive path and an elongated tongue holding segment connected with and extending out from said handle connecting segment, said blade also including a light guide having a back end located at its handle connecting segment and a front end located at the tongue holding segment, said light guide being adapted to receive light at its back end for directing the received light to its front end;
(c) first means and second cooperating means respectively forming parts of the head portion of said handle and the handle connecting segment of said blade for disengagably connecting said blade to said handle in a specific way which automatically causes said electrically conductive path defining means to engage and electrically connect together said first and second members and which, at the same time, automatically places said light guide in a predetermined position relative to the blade connecting head portion of said handle, said first means including said first and second members;
(d) an electrical light source carried by the blade connecting head portion of said handle and positioned so as to be in optical communication with the back end of said light guide when said blade is connected to said handle in said specific way;
(e) a power supply disposed within the inner chamber of said handle for energizing said light source when placed in electrical connection therewith; and
(f) circuit means for electrically connecting said light source and power supply to ground, for electrically connecting said first member to the hot side of said power supply, and for electrically connecting said second member to the hot side of said light source so that said power supply is automatically placed in electrical connection with said light source in order to energize the latter when said first and second members are electrically connected together by said electrically conductive path defining means, whereby disengagably connecting said blade to said handle in said specific way automatically causes said light source to be energized and disengagement of said blade from said handle automatically causes said light source to be deenergized, said blade connecting head portion of the handle including a third electrically conductive member electrically insulated from said first and second members and said circuit means including means for electrically connecting said third electrically conductive member to the ground side of said power supply such that when said first and third members are electrically connected across a different light source, the latter is automatically energized by said power supply, whereby a second type of blade including said second light source and means for engaging said handle in a way which electrically connects said first and third members can be connected with said handle in said last-mentioned way for automatically energizing said second light source when said first-mentioned blade is not connected with said handle.

27. A laryngoscope according to claim 26 including said second blade and wherein said second blade is configured and said electrically conductive member are positioned such that connecting said second blade to said handle in said specific way does not electrically connect said second member with said first member, whereby said first-mentioned light source remains deenergized.

28. A laryngoscope according to claim 26 wherein the blade connecting head portion of said handle is separate from said hand gripping portion, wherein said hand gripping portion includes an opening which is partially threaded and which extends into said inner chamber from one end and wherein said blade connecting head portion includes a main body having an opening therethrough and a sleeve at least partially externally threaded extending through said last-mentioned opening and into the opening in said hand gripping portion for thread connection with the latter, said sleeve including means for engaging said main body so as to disengagably connect the latter with said hand gripping portion, said sleeve also containing said first member and means for placing the latter in electrical engagement with said power supply.

29. A laryngoscope, comprising:
(a) a laryngoscope blade having a handle connecting segment and an elongated tongue holding segment connected with and extending out from said handle connecting segment;
(b) a handle including
(i) a hand gripping portion having a top end, a bottom end, an inner chamber for containing a power supply and an opening which extends from its top end into said chamber and which includes a threaded segment along its length, and
(ii) a blade connecting head portion including a main body defining an opening therethrough and an elongated stem including an externally threaded segment configured to extend through the opening in said main body and into the opening in said hand gripping portion such that the threaded segments of the two cooperate with one another for connecting the stem to the hand gripping portion, said stem also including shoulder means engaging said main body for connecting the latter with said hand gripping portion, whereby said blade connecting head portion in its entirety is disengagably connectable with and disengagable from said hand gripping portion, said shoulder means forming part of said stem including a shoulder larger than the opening in the main body of said blade connecting head portion and located at the top end of the stem, said shoulder including an opening through which a portion of said electrically conductive member extends and a slotted top surface for receiving a screwdriver;

(c) means carried partially by said handle and partially by said blade including a power supply within said inner chamber for producing a beam of light in a predetermined direction relative to the tongue holding segment of said blade when said blade is connected with said handle in a specific way; and (d) first and second cooperating means respectively forming parts of the head portion of said handle and the handle connecting segment of said blade for disengagably connecting said blade to said handle in said specific way so as to cause said beam to be produced.

30. A laryngoscope according to claim 29 wherein said beam producing means includes an elongated electrically conductive member which is disposed within said sleeve and which has a bottom end in electrical engagement with said power supply and a top end accessible from the top end of said sleeve.

31. A laryngoscope according to claim 29 wherein said hand gripping portion of said handle has means including a number of disengagable components for receiving a laryngoscope blade different in design than said first-mentioned blade without utilizing said blade connecting head portion, one of said components serving to aid in connecting said blade connecting head portion with said hand gripping portion when the former is used.

32. A laryngoscope comprising:
(a) a handle including an elongated hand gripping portion and a blade connecting head portion;
(b) a disposable blade separate from said handle and including a handle connecting segment and an elongated tongue holding segment connected with and extending out from said handle connecting segment;
(c) means carried partially by said handle and partially by said blade for producing a beam of light in a predetermined direction relative to the tongue holding segment of said blade when said blade is connected with said handle in a specific way, said beam producing means including a light source, a power supply and circuit means for electrically connecting said power supply to said light source for energizing the latter and producing said beam; and
(d) first and second cooperating means respectively forming parts of the head portion of said handle and the handle connecting segment of said blade for disengagably connecting said disposable blade to said handle in said specific way for the first time so as to cause said circuit means to electrically connect said power supply to said light source to produce said beam and so as to damage a component of said circuit means sufficient to discourage its use a second time without preventing it from being used in the proper way the first time.

33. A laryngoscope comprising:
(a) a handle including an elongated hand gripping portion and a blade connecting head portion;
(b) a disposable blade separate from said handle and including a handle connecting segment and an elongated tongue holding segment connected with and extending out from said handle connecting segment;
(c) means carried partially by said handle and partially by said blade for producing a beam of light in a predetermined direction relative to the tongue holding segment of said blade when said blade is connected with said handle in said specific way, said beam producing means including a power supply and a light source carried by said handle and a light guide fixedly held by and extending between said head connecting and tongue holding segments of said blade so as to be placed in optical alignment with said light source for directing said beam in said predetermined direction when said blade is connected to said handle in a specific way;
(d) first and second cooperating means respectively forming parts of the head portion of said handle and the handle connecting segment of said blade for disengagably connecting said disposable blade to said handle in said specific way for the first time so as to cause said beam to be produced and so as to damage a component of said disposable blade sufficient to discourage its use a second time without preventing it from being used in the proper way the first time; and
(e) an additional blade having its own tongue holding segment carrying its own light source and a handle segment carrying its own light source and a handle connecting segment including means for disengagably connecting said additional blade to said handle in a way which places said last-mentioned light source in circuit with said power supply without placing said first-mentioned light source in electrical circuit with said power supply.

34. A disposable blade for use as part of a laryngoscope which also includes a handle having an elongated hand gripping portion, a blade connecting head portion, a light source and a power supply for energizing said light source, said disposable blade comprising:
(a) a handle connecting segment including means designed to cooperate with the blade connecting head portion of said handle for disengagably connecting the blade to the handle in a specific way so that when said blade is connected to said handle in said specific way for the first time the two form an electrical circuit for electrically connecting said power supply to said light source for energizing the latter and, at the same time, a component forming part of said blade and of said circuit is damaged sufficient to discourage use of the latter a second time, but without preventing it from being used in the proper way the first time,
(b) an elongated tongue holding segment connected with and extending out from said handle connecting segment; and
(c) means carried by said blade and designed to cooperate with said handle for directing the beam of light in a predetermined direction relative to said tongue holding segment.

35. A laryngoscope, comprising:
(a) a handle having a hand gripping portion and a blade connecting head portion, said head portion including first and second electrically conductive members and dielectric means for electrically insulating said members from one another;
(b) a laryngoscope blade separate from said handle and having a handle connecting segment including means defining an electrically conductive path and an elongated tongue holding segment connected with and extending out from said handle connecting segment;

(c) first and second cooperating means respectively forming parts of the head portion of said handle and the handle connecting segment of said blade for disengagably connecting said blade to said handle in a specific way which automatically causes said electrically conductive path defining means to engage and electrically connect together said first and second members;

(d) an electrical light source carried by said handle;

(e) a power supply carried by said handle for energizing said light source when placed in electrical connection with the latter; and (f) circuit means including said first and second electrically conductive members electrically connected with said light source and power supply in a predetermined way and also including said electrically conductive path defining means for automatically placing said power supply in electrical connection with said light source in order to energize the latter when said first and second members are electrically connected together by said path defining means, whereby disengagably connecting said blade to said handle in said specific way automatically causes said light source to be energized, said first cooperating means for disengagably connecting said blade to said handle including a third electrically conductive member electrically insulated from said first and second members and said circuit means including means for connecting said first and third members in circuit with said power supply such that when said first and third members are electrically connected across a second light source carried by a different laryngoscope blade, the second source is automatically energized by said power supply, whereby said different blade can be connected to said handle for electrically connecting said first and third members together.

36. A laryngoscope comprising: a handle including a first light source and power source means; a first blade having means including a second light source thereon; means forming part of said handle and part of said first blade for mounting the first blade with said handle in a way which causes said power source means to energize said second light source without energizing said first light source; and a second blade carrying a light guide but no light source and having means for mounting the second blade with said handle in a way which causes said power source means to energize the first light source while placing said light guide in optical communication with said last-mentioned light source.

37. A laryngoscope comprising: a handle including a light source, first electrical contact means fixedly electrically connected with said light source, a power supply, second electrical contact means fixedly electrically connected with said power supply and means electrically insulating said contacts from one another; and a blade including an electrical conductive means and means for mounting the blade with said handle in a way which automatically causes said electrical conductive means to engage said first and second contact means in order to electrically connect them together whereby to electrically connect said power supply with said light source for energizing the latter.

* * * * *